United States Patent [19]

Littleford

[11] 4,401,127

[45] * Aug. 30, 1983

[54] STABLE ELECTRODES FOR ENDOCARDIAL PACING

[76] Inventor: Philip O. Littleford, 251 Salvador Sq., Winter Park, Fla. 32789

[*] Notice: The portion of the term of this patent subsequent to Nov. 9, 1999 has been disclaimed.

[21] Appl. No.: 231,130

[22] Filed: Feb. 3, 1981

Related U.S. Application Data

[63] Continuation-in-part of Ser. No. 168,742, Jul. 14, 1980, Pat. No. 4,357,947.

[51] Int. Cl.³ .............................................. A61N 1/04
[52] U.S. Cl. ................................. 128/786; 128/419 P
[58] Field of Search ........................... 128/784–786, 128/419 P, 348, 349, 214 R, 214.4, 642, DIG. 9, 772; 604/100, 177

[56] References Cited

U.S. PATENT DOCUMENTS

| | | | |
|---|---|---|---|
| 3,390,977 | 6/1975 | Wilson | 128/785 X |
| 3,670,727 | 6/1972 | Reiterman | 128/214 R |
| 3,729,008 | 4/1973 | Berkovits | 128/419 P X |
| 3,782,381 | 1/1974 | Winnie | 128/349 R X |
| 3,880,169 | 4/1975 | Starr et al. | 128/785 |
| 3,939,843 | 2/1976 | Smyth | 128/786 |

FOREIGN PATENT DOCUMENTS 375855  7/1907  France ........................... 128/349 R

*Primary Examiner*—Lee S. Cohen
*Attorney, Agent, or Firm*—Duckworth, Allen, Dyer & Pettis

[57] ABSTRACT

Electrode catheters for rapid endocardial insertion and for interconnection with a pacemaker include a flexible conductor having an outer, electrically insulating sheath about the conductor with a curve, bend or other portion at the distal end of the catheter. A wing extends laterally from the catheter at the proximal end, and has an established relationship between the lateral direction of the wing and the curve, bend or other portion allowing the physician to control the orientation of the distal end after insertion to permit the desired positioning of the curve, bend or other portion within the heart. The wing may then be used to stabilize the electrode by taping to the patient's skin.

12 Claims, 11 Drawing Figures

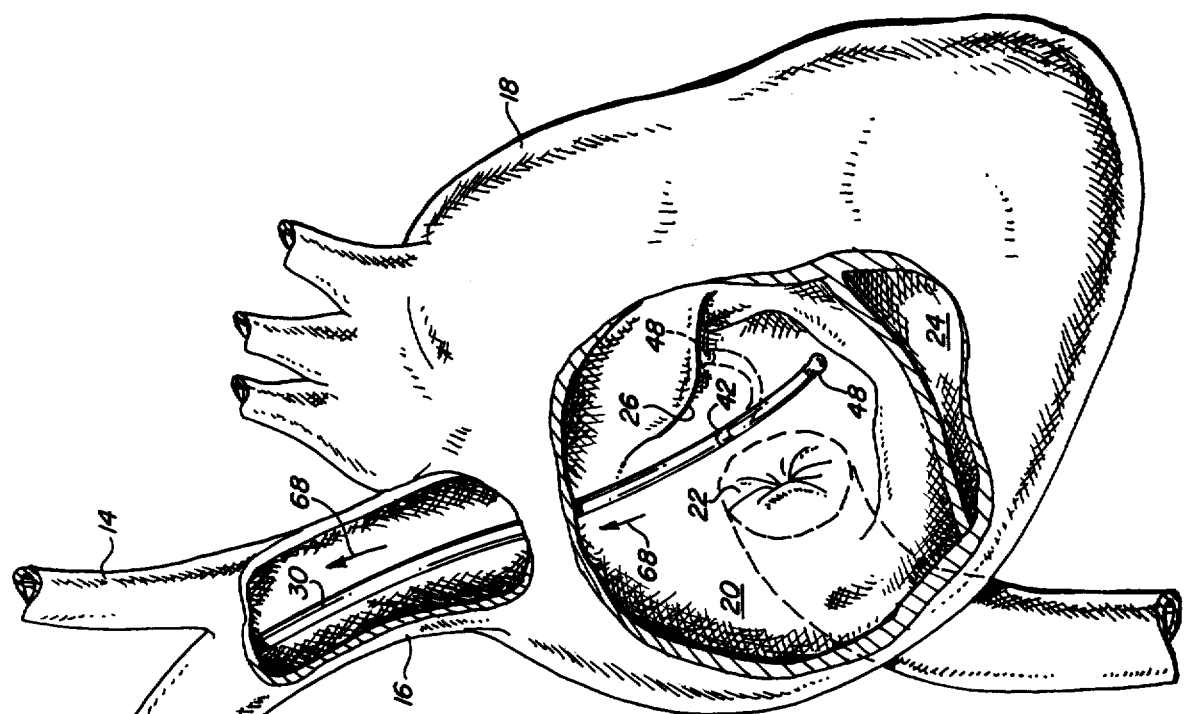
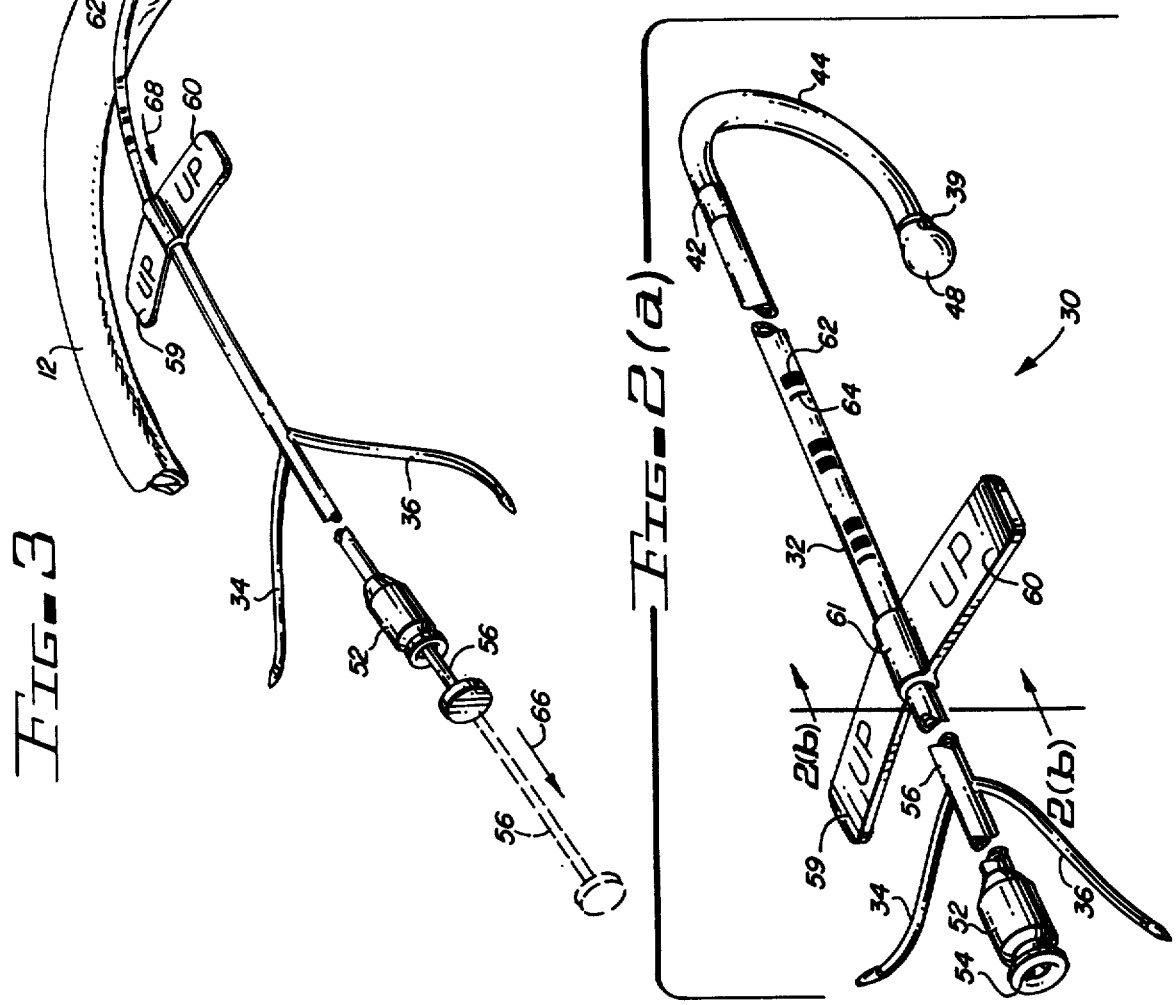

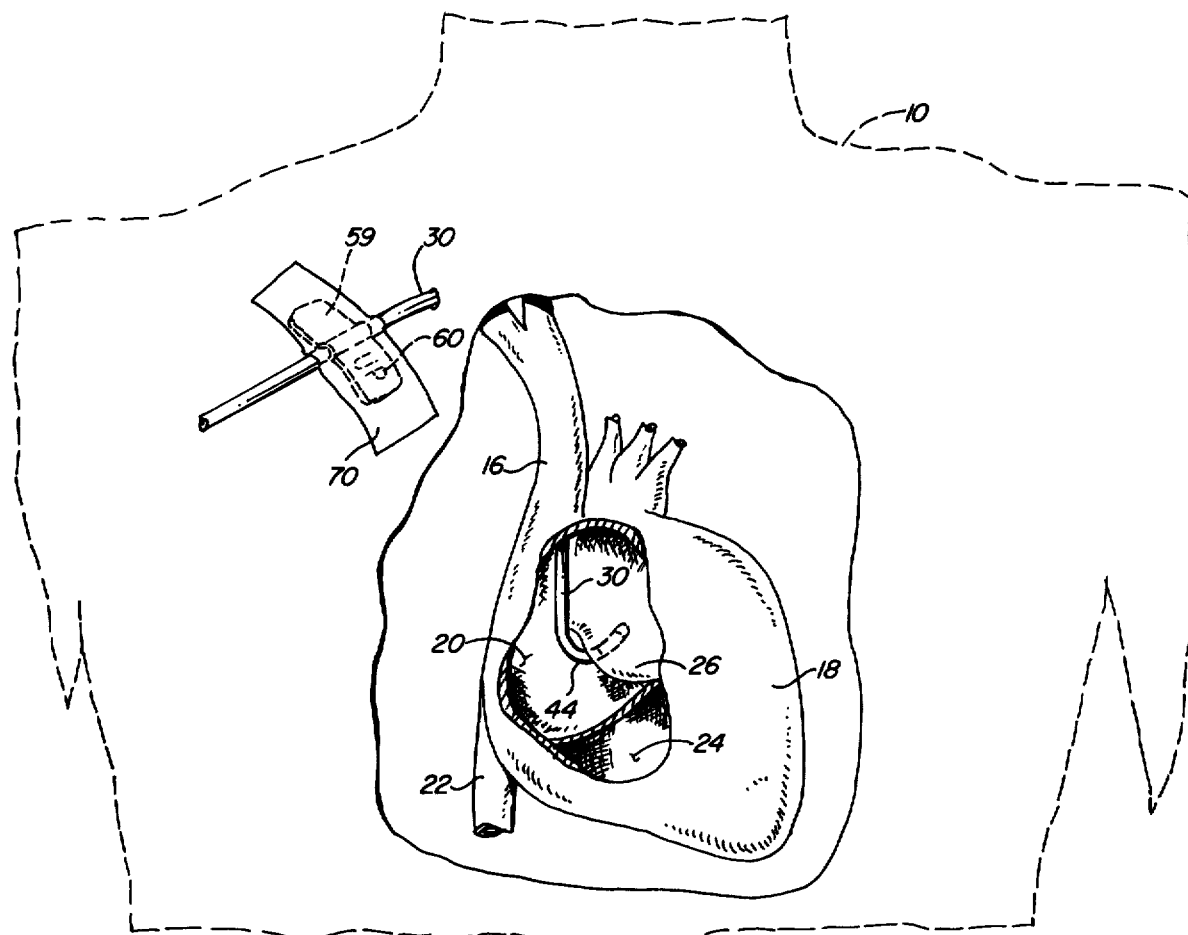
FIG_4
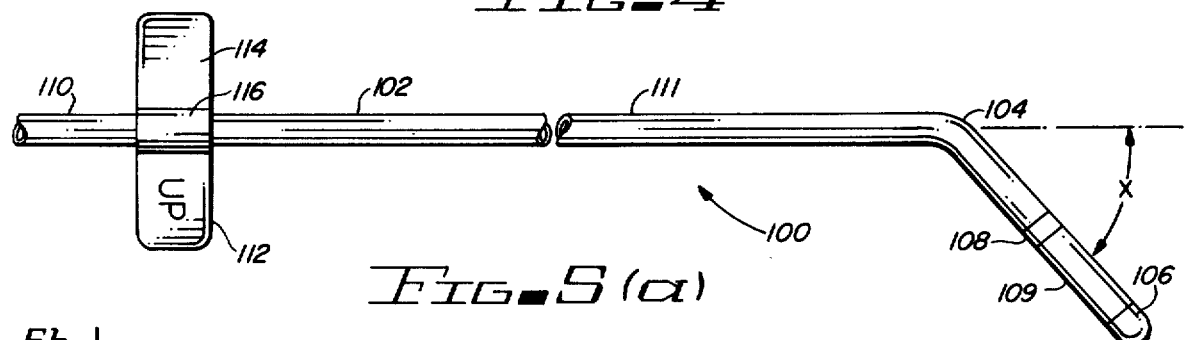
FIG_5(a)
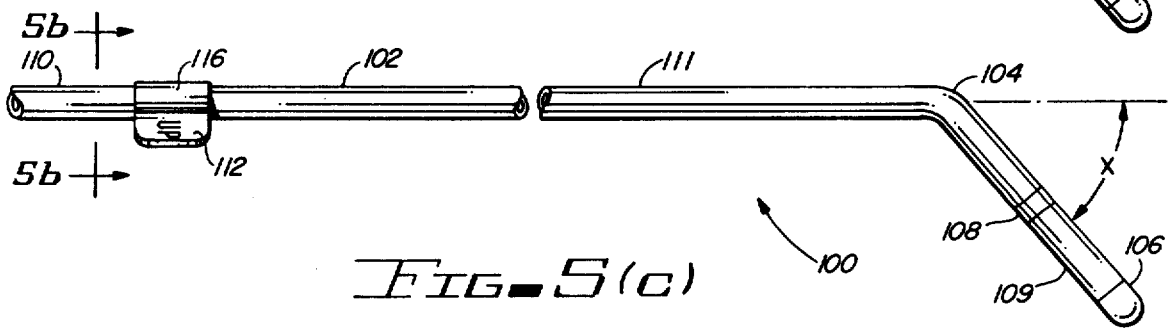
FIG_5(c)

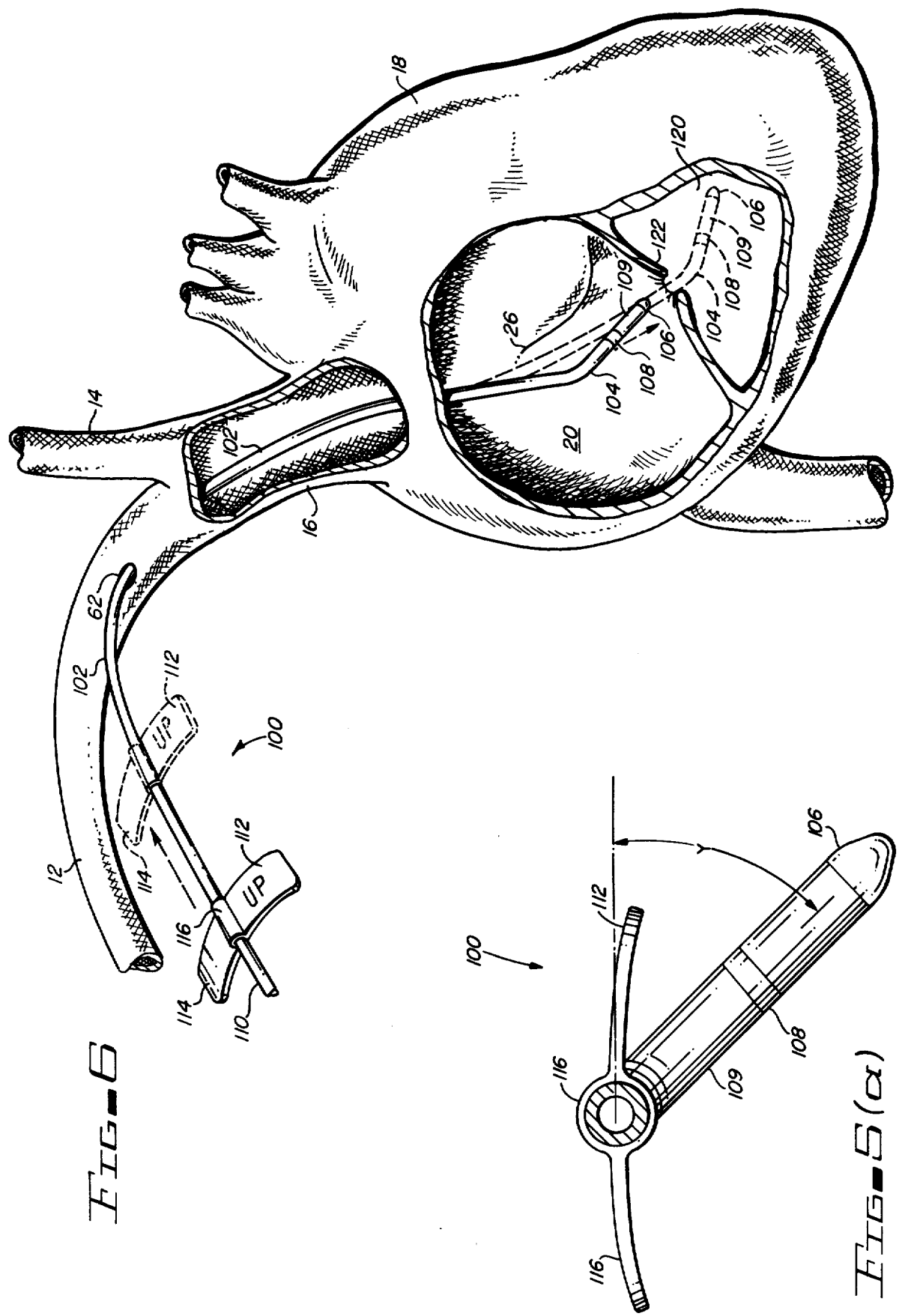

STABLE ELECTRODES FOR ENDOCARDIAL PACING

This application is a continuation-in-part of Application, Ser. No. 168,742, filed July 14, 1980, now U.S. Pat. No. 4,357,947.

The present invention relates generally to medical and surgical devices and methods, and in particular, relates to electrodes which are designed to be inserted through the circulatory system and into a patient's heart for purposes of permitting an artificial electronic stimuli to pace the patient's heart.

The term "pacemaker" generally applies to devices in a family of electronic products which are electrically connected through an electrode for providing electronic pacing impulses to a patient's heart.

One type of pacemaker, referred to as a permanent pacemaker, is packaged in a small, portable container and is usually implanted under the patient's skin in a major surgical technique. Pacemaker implants are carried out in an operating room or similar facility equipped with a fluoroscope, which permits the attending physician to precisely position the extremity of the permanent pacemaker electrode in a desired location in the heart.

Another type of pacemaker provides temporary pacing stimuli to the patient, and employs an electrode which is designed to be inserted by a physician in a rapid manner while the patient is in an emergency room, intensive care unit, catheter laboratory or similar facility.

Generally, a fluoroscopic unit is used during insertion of a temporary pacing electrode, but occasionally in emergency situations, "blind insertion" has been attempted, but with limited success.

It is well known that the heart may be effectively "paced" by an electronic stimulus located within the right atrium. However, it is very difficult to locate the extremity of an electrode in an appropriate location which is stable in the right atrium, even with the benefit of fluoroscopy. Without the benefit of fluoroscopy (as during the blind insertion of a temporary pacing electrode under the emergency circumstances described above), it has been heretofore unknown to insert a temporary pacing electrode in the right atrium. Because of the inability to effectively locate an electrode within the atrium in a stable manner, most pacing electrodes (both temporary and permanent) are inserted in the right ventricle, which offers stable positioning. However, it is also difficult to manipulate a pacing electrode through the tricuspid valve into the right ventricle for ventricular pacing without fluoroscopy.

In my U.S. Pat. No. 4,166,469, issued Sept. 4, 1979, I disclose apparatus and a related method for the rapid and atraumatic insertion of pacemaker electrodes through the subclavian vein.

SUMMARY OF THE INVENTION

The present invention contemplates a method and related apparatus for rapidly and accurately inserting pacing electrodes, particularly temporary pacing electrodes, into the right heart and thereafter stabilizing the electrodes. The invention is also based, in part, on the recognition that the insertion through the right subclavian vein of a curved, or "J" electrode into the right atrium will always engage the right atrium in a stable manner when the electrode is oriented and manipulated in a predetermined direction and manner; or, that the insertion through the right subclavian of an electrode having an appropriately oriented bend at the distal end will pass through the tricuspid valve into the right ventricle.

More particularly, the present invention contemplates a pacing electrode including a flexible conductor having an outer, electrically insulating sheath about the conductor, the conductor and the sheath forming a curve or bend at the distal end with the conductor having an electrical terminal along the distal end, the terminal adapted for making electrical endocardial contact. Means are further provided along the sheath for indicating the orientation of the curve or bend after the distal end has been inserted into the heart, and for stabilizing the electrode after electrical contact has been properly established between the terminal and the heart.

In a preferred embodiment of the electrode in accordance with the present invention, the orienting and stabilizing means is dimensioned along the sheath at a position outside the patient's body when the distal end has been inserted into the heart. Suitably, the orienting and stabilizing means comprises a wing extending laterally from the sheath, the lateral direction of the wing indicating the orientation of the curve or bend at the distal end. One side of the wing is provided with means for indicating which side of the wing should be facing away from the patient. The desired orientation will be obtained in accordance with the present invention when the wing lies flat against the patient's skin, with the "up" indicating means properly positioned. In the case of an atrial electrode, the distal end forms a "J" shaped flexible curve, the plane of the curve being normal to the plane of the wing. In the case of a ventricular electrode, the distal end forms a bend, the plane of which is disposed at an angle of about 45° or less with respect to the plane of the wing.

DESCRIPTION OF THE DRAWINGS

FIG. 2(a) is a front perspective view, partially cut away, illustrating an electrode in accordance with the present invention.

FIG. 3 is a front view of the human heart, the subclavian and cephalic veins and their connection to the superior vena cava, with portions of the superior vena cava and the heart cut away to illustrate the manner in which an atrial electrode in accord with the present invention is utilized.

FIG. 4 is a perspective view illustrating the manner in which an electrode in accordance with the present invention is stabilized after insertion.

FIGS. 5(a), (b) and (c) are top, side and end views, respectively, of a ventricular electrode in accordance with the present invention.

FIG. 6 is a perspective front view of the human heart, illustrating the manner in which the ventricular electrode of FIGS. 5(a)-(c) is utilized.

DETAILED DESCRIPTION OF THE PREFERRED EMBODIMENTS

1. Atrial Electrode

A preferred embodiment of an atrial electrode in keeping with the present invention will now be described with reference to FIGS. 1-4. While one particular structural arrangement of a bipolar temporary electrode in accordance with the present invention is shown and described, it will be understood by those skilled in the art from the detailed description set forth below that the design may be adapted for unipolar electrodes as well as permanent electrodes, and that various modifications may be made in the design without departing from the spirit and scope of the present invention.

Figure 1A:
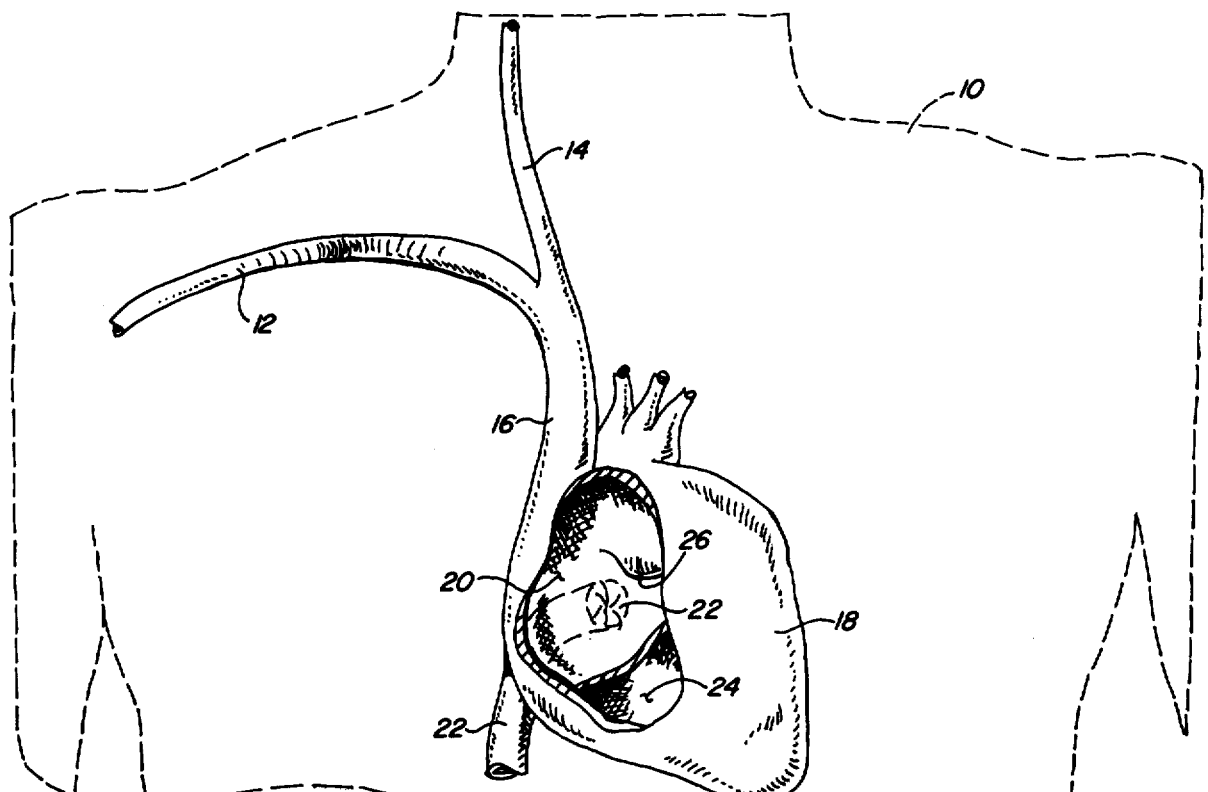
FIG. 1(a) is a front view of the human anatomy, particularly illustrating the human heart with a portion cut away to show the inside of the right atrium and a portion of the right ventricle.

With particular reference to FIGS. 1(a) and (b), there is illustrated a human body 10, the right subclavian vein 12, the cephalic vein 14 and the superior vena cava 16. The drawing of FIG. 1 is fanciful in nature, it being understood that the drawing is not to scale, but serves only to illustrate the functional relationships of the heart and the associated circulatory system.

Element 18 refers to the heart, including the right atrium 20, the right ventricle 24, and the inferior vena cava 22. The wall between the right atrium 20 and the right ventricle 24 is cut away in the area where the tricuspid valve would normally be located for purposes of permitting illustration of the right ventricle. As is known, blood from the arms, head and body flow into the right atrium 20 via the superior vena cava 16 from, amont others, the subclavian and cephalic veins 12 and 14. Blood from the trunk and legs enters the right atrium 20 via the inferior vena cava 22.

As is also known, there is a portion of the right atrium known as the right atrial appendage, identified as element 26 in FIG. 1(a). The right atrial appendage 26 is a small ear-like appendage forming a pocket located anteriorly and superiorly on the right atrial wall, the inner surface of which is particularly susceptible to pacing.

Figure 1B:
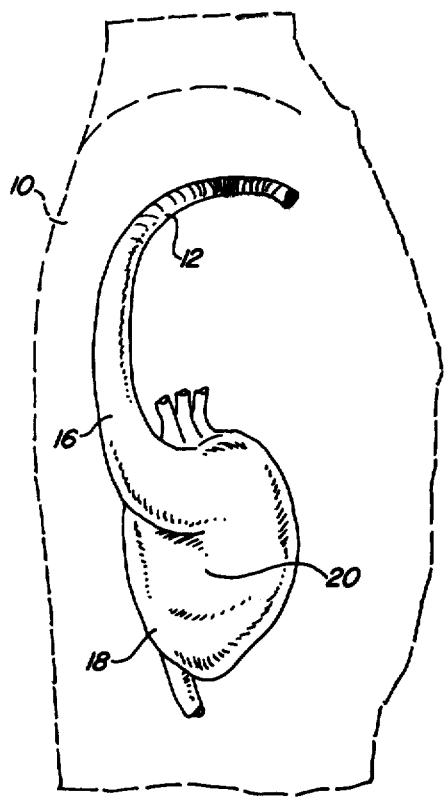
FIG. 1(b) is a side view illustrating a portion of the human anatomy, and specifically illustrating the curvature of the subclavian vein as it enters and connects with the superior vena cava.

Noting FIG. 1(b), it is seen that the curvature of the subclavian vein to the connection with the superior vena cava 16 is not flat, as it appears in FIG. 1(a); but rather is curved toward the rear of the patient's body, i.e. in the direction toward the spinal column, coming from the forward surface of the body 10.

Reference is now made to FIGS. 2(a), (b) and (c), which disclose a temporary atrial electrode in accordance with the present invention.

The electrode, referred to generally by the reference numeral 30, includes a flexible, electrically insulated sheath 32 with a pair of concentric conductors 34, 36 surrounding a central lumen 38 which may, though not necessarily, extend through the electrode 30 to the distal end 39. Each of the conductors 34, 36 are insulated by a layer of insulating material (not numbered—see FIG. 2(c)).

Each of the conductors 34, 36 are exposed at the surface of the outer insulating sheath 32, in order to permit electrical contact in the heart when the electrode 30 is in place. By way of example, conductor 34 may have a surface terminal 42 and inner concentric conductor 36 may have a surface terminal 48 at the distal extremity 39. Typically, the outer conductor 34 will serve to shield the inner conductor 36, and the inner conductor will therefore be relied upon to provide pacing signals at the distal extremity 39 of the electrode 30. In accordance with a preferred embodiment of the present invention, the terminal 48 consists of a spherical conductor connected electrically with the inner conductor 36.

Referring again to FIG. 2(a), the proximal extremity of the electrode 30 includes a hub 52 having an opening 54 which communicates with the central lumen 38. Each of the concentric conductors 34, 36 include external portions which likewise exit the electrode 30 at the proximal end 50, typically in the manner shown in FIG. 2(a). As is well known, the proximal extremities of each conductor 34, 36 may be connected to a temporary pacemaker (not shown).

Figure 2B:
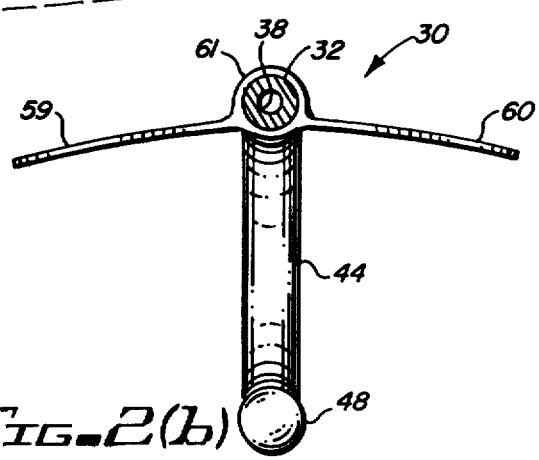
FIG. 2(b) is a front sectional view of the electrode of FIG. 2(a), along the line 2(b)—2(b).
Figure 2C:
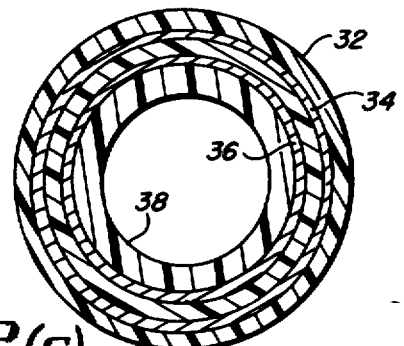
FIG. 2(c) is an enlarged illustration of the end section of the view of FIG. 2(b).

As is shown on the right-hand side of FIG. 2(a), the electrode 30 is provided with a somewhat gentle curve 44 between the terminal 42 and the distal extremity 39 which permits the conductor terminal 48 at the distal extremity 39 to be pointed in a direction approximately 180° from the direction of the electrode 30, and in a plane substantially parallel with the plane of the electrode; that is to say, when the main body of the electrode 30 is lying on a flat surface, the curved portion 44 and the distal extremity 39 are likewise lying in the plane of the same flat surface (see FIG. 2(b)). The insulative sheath 32, including the insulative materials between the conductive electrodes 34, 36 are of a material which has an elastic memory so that when the curved portion of the distal extremity 39 of the electrode 30 is straightened, the curved portion at the distal extremity 39 will thereafter resume its curved configuration. A number of conventional silastic and other non-toxic plastic materials are suitable for this purpose.

Straightening of the curve 44 of the electrode 30 during insertion may be accomplished by simply manipulation with the hands, or with a stylet 56 having an outer diameter sufficiently small to permit it to pass through the opening 54, down the central lumen 38 to straighten the curved end and hold the entire electrode, including the distal extremity 39, straight. The stylet 56 must be sufficiently flexible to permit the electrode to pass through the subclavian vein 12, the superior vena cava 16 and into the right atrium 20.

In accordance with the present invention, the electrode 30 is provided with means for indicating the relative position of the curved distal extremity 39 with respect to the axial direction of the electrode 30 and the plane in which the electrode and the curved extremity lies. In the embodiment shown in FIG. 2(a), the indicating means in this regard comprises a pair of flat, relatively flexible plastic wings 59, 60 which are joined by a sleeve 61 to the proximal extremity and extend laterally from the outer insulated sheath 32. As is shown in FIG. 2(a), the indicating wings 59 and 60 extend generally perpendicular to the plane of the curve 44, the distal extremity 39 and the main body of the electrode 30. As shown in FIGS. 2(a) and (b), the wings 59, 60 are curved slightly downward and include the notation "UP" on the upper side intended to be away from the patient's body, as described further below.

The electrode 30 further includes means for indicating the distance along the insulating sheath 32 from the curve in the distal extremity 39. In the embodiment of FIG. 2(a), this distance indicating means comprises a series of gradations along the insulating sheath 32 forward of the indicating wings 59, 60 in the direction of the curve of the extremity 39. Typically, the gradations may include wide gradations 62 and thin gradations 64, each wide gradation indicating a 10 cm. segment and each thin gradation indicating a 5 cm. segment; thus, an individual marking of two wide gradations and one thin gradation would indicate a 25 cm. distance from the curved end.

The manner in which the electrode of the present invention is employed for insertion through the right subclavian vein and into the right atrium without the use of fluoroscopy will now be described with reference to FIG. 3.

Before beginning the technique of inserting the electrode 30 in the manner hereinafter described, the patient is properly prepared and normal sterilization techniques are observed.

Initially, a puncture is made through the patient's skin in the area adjacent the clavicle so as to pass a small, thin-walled 18 gauge needle into the right subclavian vein 12, to thereafter permit the introduction of a removable introducer in the manner which is clearly described in my U.S. Pat. No. 4,166,469. Because the technique for inserting a removable introducer sleeve into the right subclavian vein is clearly described in the specification of that patent, it is incorporated here by reference.

Once that sleeve is properly inserted, the curve 44 of the electrode 30 is straightened. The electrode 30 is then inserted down a removable introducer sleeve (not shown in FIG. 3, but see sleeve 56 in FIG. 11 of my aforementioned U.S. Pat. No. 4,166,469). Once the straightened distal extremity 39 of the electrode is inserted down the introducer sleeve into the subclavian vein 12, it is then manipulated through the superior vena cava 16 and into the right atrium 20. The removable introducer sleeve is then removed by peeling it away, allowing the wings 59, 60 to be positioned close to the entrance site into the subclavian vein 12.

At this point in the technique, the electrode 30 has been inserted as desired so that the straightened distal extremity 39 is positioned in the right atrium 20. It will be understood that the insertion technique thus far described leaves the indicating wings 59 and 60 exteriorly of the patient's skin. As a next step, the attending physician ensures that the indicating wings 59 and 60 are lying substantially parallel to the plane of the patient's skin, and with the words "UP" facing the physician. If a stylet is being used, the stylet is removed. In either event, the curve 44 resumes it normal, curved configuration, as is shown by dotted lines on the right side of FIG. 3.

If the physician has inserted the electrode a sufficient distance into the subclavian vein 12 (and down the superior vena cava 16 and into the right atrium 20), as is determined by reference to the indicating marks 62, 64 along the outer sheath 32, and if the indicating wings 59 and 60 are positioned in the manner described above, then the curved distal extremity 39 will assume a direction in which the terminal electrode 48 is pointed directly upward toward the right atrial appendage 26. This is because of the unique relationship of the curvature from the right subclavian vein 12, running down the superior vena cava 16 and into the right atrium 20, as is clearly shown in FIG. 1(b). As was noted previously, the subclavian vein 12 actually curves slightly backward toward the spinal column as it communicates with the superior vena cava 16, the superior vena cava communicating with the right atrium 20 at the rear of the heart 18. Thus, the indicating wings 59 and 60 and the curvature of the curve 44 are oriented such that when the indicating wings 59 and 60 are positioned substantially parallel to the patient's skin and with the "UP" side facing the physician, then the curve 44 at the distal extremity 39 is formed so that the conductive terminal 48 is pointed in the desired manner in the pocket under the right atrial appendage 26.

Next, the attending physician connects the conductors 34, 36 to the pacemaker pulse generator and then pulls the electrode 30 slightly outward away from the puncture wound in the skin and away from the subclavian vein 12, as is shown by the arrows 68 in FIG. 3. The electrode 30 may be withdrawn in this manner a distance of between 1 to 7 centimeters, as determined by reference to the gradations 62, 64 so as to ensure that the conductive terminal 48 engages the surface underneath the right atrial appendage 26. Typically, the physician will ascertain appropriate electrode "capture" by referring to the pulse generator. Because of the spherical configuration of the terminal 48, that terminal makes a broad electrical contact with the wall of the right atrium 20 in the pocket of the appendage 26, but without damage to the wall. The terminal 48 stays in the desired location because of the tension at the curve 44, despite continual movement of the atrial wall.

It will be appreciated that the manipulative steps described above can take place without the benefit of fluoroscopy, thus permitting a temporary electrode to be placed easily and quickly into the right atrium 20 for purposes of obtaining the benefits of physiological atrial pacing under emergency or temporary conditions.

After the electrode 30 has been inserted and the terminal 48 engaged in the desired manner, the electrode may then be stabilized. Noting FIG. 4, this is accomplished by placing the wings 59, 60 flat against the patient's skin near the puncture wound and fastening against the patient's skin by a strip of tape 70. During atrial pacing, the curve 44 and the distal end 39 will be subjected to significant movement and thus, torque, as illustrated by the arrows adjacent the curve 44 in FIG. 4. However, the electrode 30 will be stabilized against losing its position because of the tape 70.

2. Ventricular Electrode

A preferred embodiment of a ventricular electrode in accordance with the present invention will now be described with reference to FIGS. 5(a) through (c) and 6. While one particular structural arrangement of a bipolar temporary ventricular electrode is shown and described, it will be understood that the design may be adapted for unipolar electrodes, as well as permanent electrodes, and that various modifications may be made in the design without departing from the present invention.

Noting FIGS. 5(a), (b) and (c), the ventricular electrode, referred to by the reference numeral 100, includes a pair of conductors spaced by an insulating sheath 102. The conductors are connected to terminals 106 and 108 at the distal end of the electrode 100. While the conductors are not shown or numbered in FIGS. 5(a), (b) and (c), the manner in which such conductors extend through the insulating sheath 102 are adequately illustrated and described above with reference to FIGS. 2(a) and 2(c). Preferably, the electrode terminal 106 is formed of a cylinder having a hemispherical curved tip at the extremity thereof. The electrode 108 is formed of a metal band flush with the surface of the insulating sheath 102.

In accordance with the present invention, the electrode 100 includes a bend 104 approximately 6 to 10 centimeters from the distal end at terminal 106, in the direction away from the distal end toward the proximal end 110. As is shown in FIGS. 5(a) and (c), the bend 104 is made so as to extend the distal portion of the electrode 100 in a lateral direction away from the axial direction of the main body portion of the electrode 100 at an angle represented by the letter X in those figures. Preferably, the angle X is approximately 60°. For reference purposes, the term "distal portion" is used to describe that portion of the electrode between the distal terminal 106 and the bend 104, and is referred to generally by the reference numeral 109. In a like manner, the term "body portion" refers to that portion of the electrode 100 between the proximal end 110 and the bend 104, and is referred to generally by the reference numeral 111.

The electrode 100 includes means for indicating the direction of the bend of the distal portion 109 and for stabilizing the entire electrode 100 after insertion. In accordance with the present invention, the orientation indicating and stabilizing means comprises a pair of wings 112, 114 fixed by a collar 116 to the outer periphery of the insulating sheath 102 adjacent the proximal end 110. Preferably, the wings 112, 114 are fixed to the sheath 102 between 30-40 centimeters from the end of the terminal 106. The lateral direction of extension of the wings 112, 114 are pre-determined so as to indicate the orientation of the distal portion 109 away from the bend 104. Noting FIG. 5(b), the lateral direction of the distal portion 109 is further specifically designed to extend at an angle Y out of the plane of the wings 112, 114 and away from the "UP" side. Preferably, the angle Y is between 0°-45° with respect to the plane of the wings 112, 114.

With the distal portion 109 angularly disposed away from the body portion 111 by the angles X and Y and the length noted above, the ventricular electrode 100 is particularly suited for insertion through the right subclavian vein 12, through the superior vena cava 16 and into the right atrium 20 of the human heart. With the wings 112, 114 lying flat against the patient's skin and with the notation "UP" facing away from the patient's skin, the bend 104 will point the distal portion 109 in the direction of the tricuspid valve, and thereafter permit the distal portion 109 to extend through the tricuspid valve as the electrode 100 moves toward the right ventricle. This is clearly shown in FIG. 6, which illustrates the manner in which the electrode 100 of FIGS. 5(a) through (c) is inserted into the right ventricle of the patient's heart. With reference to FIG. 6, there is shown the heart 18, the communicating superior vena cava 16, and the right subclavian vein 12. The heart includes the right atrium 20 and the right ventricle 120 separated by the tricuspid valve 122.

The electrode 100 is initially inserted in the right subclavian vein 12 underneath the clavicle, in the manner previously described. During insertion, the wings 112 and 114 are positioned with the "UP" indicator facing upward away from the patient's skin. (Of course, the electrode 100 of FIGS. 5(a) through (c) and FIG. 6 include a hub 52 which is omitted in FIGS. 5(a) through (c) and FIG. 6.) At the time the electrode 100 is inserted into the vein through the introducer, the bent distal portion 109 is straightened by hand, or with a stylet in the manner described above with reference to the atrial electrode 30. To this end, the conductor and insulating sheath 102 are formed of a flexible material similar to the atrial electrode.

After the bend 104 passes out of the superior vena cava 16 and into the right atrium 20, the bend 104 causes the distal portion 109 to extend in the direction of the tricuspid valve 122. Because of the dimensions and angular relationship described specifically above, the distal portion 109 will lie slightly across the tricuspid valve 122 and downward toward the right ventricle 120. As the tricuspid valve opens and closes, the electrode 100 is gently moved forward through the right atrium until such time as the distal terminal 106 comes in contact with, and passes through the tricuspid valve 122. While the normal path of an unbent ventricular electrode when passing into the right atrium would be toward the inferior vena cava or the right atrial wall, the bend 104 in the electrode 100, as shown in FIG. 6, causes the distal terminal 106 to point downward and through the tricuspid valve 122. This dimensional and angular relationship then permits the distal portion 109 to pass through the tricuspid valve 122, and into the right ventricle 120. The electrode 100 is then moved forward an additional distance to permit the distal terminal 106 to make appropriate electrical contact within the right ventricle 120, as is determined by reference to the electrical connection between the conductors within the electrode 100 and a pacemaker pulse generator (not shown). The wings 112, 114 are thus positioned forward of their original position, as is indicated by the dotted configuration of the wings in FIG. 6. The electrode 100 may then be stabilized by placing a strip of tape across the wings 112, 114 and against the patient's skin, in the manner described above.

I claim:

1. A pacing electrode for insertion through a puncture wound into a patient's body for providing an electronic stimulus to the patient's heart, said electrode comprising:
    a flexible conductor having an outer insulating sheath, said sheath and conductor including proximal and distal ends, a body portion and distal portion, said distal portion extending into a lateral direction away from the axial direction of said body portion;
    a conductive terminal at the end of said distal portion of said conductor for electrical connection within the heart;
    means along said body portion at the proximal end of said conductor for indicating said lateral direction of said distal portion;
    means adjacent the proximal end of said sheath for interconnecting a pacemaker pulse generator to said conductor; and wherein
    said distal end of said conductor is inserted into the heart with the proximal end and said indicating means extending outside of said puncture wound, whereby said distal portion may be located in a desired position by manipulation of said proximal end and said indicating means after insertion of said distal end into the patient's heart, said indicating means comprising a wing joined to said sheath adjacent said proximal end, said wing extending away from said conductor in a fixed relation to the lateral direction of said distal portion.

2. The pacing electrode recited in claim 1 further comprising means for stabilizing said conductor.

3. The pacing electrode recited in claim 2 wherein said stabilizing means comprises a tape strip fixing said wing against the skin of the patient adjacent said puncture wound after insertion of the distal end into the patient's heart, and after manipulation of said indicating means.

4. The pacing electrode recited in claim 1 wherein said distal portion is bent away from said body portion and out of the plane of said wing.

5. A pacing electrode adapted for endocardial insertion through the superior vena cava and into the right ventricle of a patient's heart for providing electronic pacing signals, said electrode comprising:
- a flexible conductor having an outer insulating sheath, said conductor and sheath including proximal and distal ends, a body portion and a distal portion;
- a conductive terminal at the end of said distal portion of said conductor for electrical connection within the right ventricle;
- means adjacent the proximal end of said sheath and conductor for interconnecting a pacemaker pulse generator to said conductor;
- a wing fixed adjacent the proximal end of said sheath and extending along a plane away from said sheath;
- said distal portion being bent away from the axial direction of said body portion, and out of the plane of said wing; and wherein
- said conductor and wing are disposed such that said bent distal portion extends angularly toward the tricuspid valve when said conductor passes out of the superior vena cava and through the right atrium, and with said wing lying flat against the patient's skin.

6. The pacing electrode recited in claim 5 wherein said distal portion is disposed with respect to the plane of said wing at an angle of between about 0°–45°.

7. The pacing electrode recited in claim 5 or 6 wherein said distal portion is disposed with respect to the axial direction of said body portion at an angle of about 60°.

8. The pacing electrode recited in claim 5 or 6 wherein said distal portion is approximately 6 to 10 centimeters in length.

9. The pacing electrode recited in claim 5 or 6 wherein said wing is fixed to said sheath approximately 30 to 40 centimeters toward said proximal end from said distal terminal.

10. The pacing electrode recited in claim 5 or 6 further including indicia on a side of said wing indicating which side thereof faces away from the patient's skin during insertion.

11. The pacing electrode recited in claim 5 or 6 further comprising means for stabilizing said wing against the patient's skin after insertion of said conductor.

12. A pacing electrode adapted for endocardial insertion through the superior vena cava and into the right ventricle of a patient's heart for providing electronic pacing signals, said electrode comprising:
- a flexible conductor having an outer insulating sheath, said conductor and sheath including proximal and distal ends, a body portion and a distal portion;
- a conductive terminal at the end of said distal portion of said conductor for electrical connection within the right ventricle;
- means adjacent the proximal end of said sheath and conductor for interconnecting a pacemaker pulse generator to said conductor;
- a wing adjacent the proximal end of said sheath and extending along a plane away from said sheath;
- said distal portion bent out of the axial direction of said body portion, out of the plane of said wing and out of a plane normal to the plane of said wing; and wherein
- said conductor and wing are disposed such that said bent distal portion extends angularly toward the tricuspid valve when said conductor passes out of the superior vena cava and through the right atrium, and with said wing lying flat against the patient's skin.

* * * * *